United States Patent
Miyai et al.

(10) Patent No.: US 8,086,022 B2
(45) Date of Patent: Dec. 27, 2011

(54) ELECTRON BEAM INSPECTION SYSTEM AND AN IMAGE GENERATION METHOD FOR AN ELECTRON BEAM INSPECTION SYSTEM

(75) Inventors: Hiroshi Miyai, Hitachi (JP); Yusuke Ominami, Hitachinaka (JP); Yasuhiro Gunji, Hitachiota (JP)

(73) Assignee: Hitachi High-Technologies Corporation, Tokyo (JP)

( * ) Notice: Subject to any disclaimer, the term of this patent is extended or adjusted under 35 U.S.C. 154(b) by 792 days.

(21) Appl. No.: 12/179,272

(22) Filed: Jul. 24, 2008

(65) Prior Publication Data

US 2009/0026369 A1    Jan. 29, 2009

(30) Foreign Application Priority Data

Jul. 25, 2007    (JP) .................................. 2007-193244

(51) Int. Cl.
G06K 9/00    (2006.01)
G06K 9/40    (2006.01)
G01N 23/00    (2006.01)
(52) U.S. Cl. .......................... 382/145; 382/274; 250/311
(58) Field of Classification Search .................. 382/141, 382/145, 147, 149, 173, 274, 305, 307, 312; 250/306, 307, 310, 311
See application file for complete search history.

(56) References Cited

U.S. PATENT DOCUMENTS

| | | | |
|---|---|---|---|
| 5,389,787 A | 2/1995 | Todokoro et al. | |
| 6,388,747 B2 * | 5/2002 | Nara et al. | 356/394 |
| 6,476,913 B1 * | 11/2002 | Machida et al. | 356/394 |
| 6,903,821 B2 * | 6/2005 | Nara et al. | 356/394 |
| 6,919,564 B2 * | 7/2005 | Nara et al. | 850/10 |
| 7,796,801 B2 * | 9/2010 | Kitamura et al. | 382/141 |
| 2002/0024021 A1 | 2/2002 | Iwabuchi et al. | |
| 2002/0030166 A1 | 3/2002 | Hioi et al. | |

FOREIGN PATENT DOCUMENTS

| | | | |
|---|---|---|---|
| JP | 1-132132 A | 5/1989 | |
| JP | 2-142045 A | 5/1990 | |
| JP | 5-55919 A | 3/1993 | |
| JP | 5-172655 A | 7/1993 | |
| JP | 6-139985 A | 5/1994 | |
| JP | 9-288989 A | 11/1997 | |
| JP | 2002-42712 A | 2/2002 | |
| JP | 2005-24564 A | 1/2005 | |
| JP | 2005-251753 A | 9/2005 | |
| JP | 2005-251754 A | 9/2005 | |

OTHER PUBLICATIONS

Japanese Office Action dated Mar. 2, 2010 Three (3) pages.
Editor: No. 132 Committee of Japan Society for the Promotion of Science, "Electron/Ion Beam Handbook", $2^{nd}$ ed., The Nikkan Kogyo Shimbun. Ltd., 1986, pp. 622-623; including English translation of relevant portions.
Japanese Office Action dated Dec. 8, 2009 Three (3) pages.

* cited by examiner

*Primary Examiner* — Kanjibhai Patel
(74) *Attorney, Agent, or Firm* — Crowell & Moring LLP (57) ABSTRACT

An inspection system uses a scanning electron microscope that detects a high-precision electron beam image, and at the same time removes restrictions for a low sampling rate. A sampled signal is obtained by sampling an analog brightness signal generated by a secondary electron detector at a predetermined sampling rate, and contiguous digital values contained in the sampled signal are added on an N by N digital value basis to generate a digital brightness signal whose frequency is equal to 1/N of the sampling frequency. Each, digital value contained in the digital brightness signal is divided by N to generate a digital signal made of digital values having a number of bits equal to that of the sampled signal and to generate an image signal in which each digital value of the digital signal forms one pixel data.

8 Claims, 9 Drawing Sheets

| Sampling rate (Clock frequency) (f) | Sampling period (Clock period) (T = 1/f) | Frequency of digital signal after addition and average processing (fe) | Multiple (N = f/fe) | Period of digital signal after addition and average processing (Te = T × N = 1/fe) |
|---|---|---|---|---|
| 100MHz | 10ns | 100MHz<br>50MHz<br>25MHz | 1<br>2<br>4 | 10 × 1 = 10ns<br>10 × 2 = 20ns<br>10 × 4 = 40ns |
| 50MHz | 20ns | 50MHz<br>25MHz | 1<br>2 | 20 × 1 = 20ns<br>20 × 2 = 40ns |
| 25MHz | 40ns | 25MHz | 1 | 40 × 1 = 40ns |

FIG. 10

ELECTRON BEAM INSPECTION SYSTEM AND AN IMAGE GENERATION METHOD FOR AN ELECTRON BEAM INSPECTION SYSTEM

BACKGROUND OF THE INVENTION

1. Field of the Invention

The present invention relates to a technology for inspecting an appearance of samples using a scanning electron microscope.

2. Description of the Related Art

Semiconductor devices such as memories and microcomputers for use in computers and the like are manufactured by repeatedly performing a process of transferring patterns of circuits and the like formed on photomasks through exposure treatment, lithography process, etching process, and the like. In a manufacturing process of semiconductor devices, determination results of quality of the lithography and etching processes and other processes and presence of defects such as foreign matter generation significantly affect manufacturing yields of semiconductor devices. Therefore, patterns on semiconductor wafers are inspected when each manufacturing process is completed to detect early or in advance an occurrence of abnormalities or defects.

Images of high SN need to be obtained at very high speed to carry out a high-throughput and high-precision inspection so as to keep pace with increase in wafer diameters and miniaturization of circuit patterns. For this purpose, the number of irradiated electrons is secured by using large-current beams 1000 times or more that of a common scanning electron microscope (SEM), for example, 100 nA or more to maintain the high SN ratio. Further, high-speed and high-efficiency detection of secondary electrons and backscattered electrons generated by the substrate is required.

Moreover, low accelerated electron beams of 2 keV or less are used so that semiconductor substrates having an insulating film such as a resist should not be affected by being charged. This technology is described in Editor: No. 132 Committee of Japan Society for the Promotion of Science, "Electron/Ion Beam Handbook", 2nd ed., The Nikkan Kogyo Shimbun. Ltd., 1986, pp. 622-623. However, a high-resolution observation is made very difficult by an aberration due to a space charge effect caused by a large-current and low accelerated electron beam.

As a method to solve this problem, a technique to decelerate a highly accelerated electron beam immediately before a sample and to practically irradiate the sample with a low accelerated electron beam is known. For example, a technology described in Japanese Patent Application Laid-Open No. 2-142045 and Japanese Patent Application Laid-Open No. 6-139985 is known.

An inspection system using a scanning electron microscope as described above has a problem described below. When sufficient contrast cannot be obtained due to an insufficient amount of irradiation of an electron beam irradiated on a sample, it is effective to lower the sampling rate from the standard level. However, if an attempt is made to lower the sampling rate significantly, an AD converter element performing digital conversion may not be able to handle beyond the operating range. High-precision AD conversion is needed to solve this problem. A technology to cause a low-resolution AD converter to operate as a high-resolution AD converter by performing digital conversion of each piece of continuously sampled data before addition thereof is described in Japanese Patent Application Laid-Open No. 05-55919.

Japanese Patent Application Laid-Open No. 02-142045
Japanese Patent Application Laid-Open No. 06-139985
Japanese Patent Application Laid-Open No. 09-288989
Japanese Patent Application Laid-Open No. 2005-251753
Japanese Patent Application Laid-Open No. 2005-251754
Japanese Patent Application Laid-Open No. 05-55919
Editor: No. 132 Committee of Japan Society for the Promotion of Science, "Electron/Ion Beam Handbook", 2nd ed., The Nikkan Kogyo Shimbun. Ltd., 1986, pp. 622-623

SUMMARY OF THE INVENTION

The present invention has been developed in view of the above situation and an object thereof is to provide an inspection system and an inspection method using a scanning electron microscope that detects a high-precision electron beam image and at the same time, removes restrictions of an AD converter element for a low sampling rate, which are problems at this point.

According to the present invention, an analog brightness signal generated by a secondary electron detector is sampled at a predetermined sampling rate to obtain a sampled signal. Contiguous digital values contained in the sampled signal are successively added on an N by N digital value basis to generate a digital brightness signal of a frequency of 1/N of the sampling frequency. Next, each digital value of the digital brightness signals is divided by N to generate a digital signal made of digital value whose number of bits is the same as that of the sampled signal. An image signal in which each digital value of these digital brightness signals constitutes one pixel data is generated.

By dividing each of digital brightness signals whose frequency is reduced to 1/N by a number smaller than N, a digital brightness signal made of digital value whose number of bits is larger than that of the sampled signal is generated. An image signal in which each digital value of these digital brightness signals constitutes one pixel data is generated.

According to the present invention, an inspection system using a scanning electron microscope that detects a high-precision electron beam image and at the same time, removes restrictions for a low sampling rate, which presents a problem at this point, of an AD converter element, and an inspection method can be provided.

DETAILED DESCRIPTION OF THE PREFERRED EMBODIMENTS

An exemplary configuration of an SEM (scanning electron microscope) inspection system according to the present invention will be described with reference to FIG. 1. An SEM inspection system 1 in the present embodiment has an inspection chamber 2, and the inspection chamber 2 has an electron-optical apparatus 3, a light microscope 4, and a sample chamber 8.

The electron-optical apparatus 3 has an electron gun 10, an extractor electrode 11 of an electron beam, a condensing lens 12, a blanking deflector 13, an aperture 14, a scan deflector 15, an objective lens 16, a conical reflector 17, an ExB deflector 18, and a secondary electron detector 20. The blanking deflector 13 deflects an electron beam 19 to the outside of an opening of the aperture 14. If necessary, irradiation of a sample 9 with the electron beam 19 can thereby be avoided. The ExB deflector 18 bends a trajectory of secondary electrons by both an electric filed and a magnetic field without affecting the trajectory of the electron beam 19.

The light microscope 4 has a white light source 40, an optical lens 41, and a CCD camera 42 and is arranged near the electron-optical apparatus 3. The electron-optical apparatus 3 and the light microscope 4 are arranged sufficiently apart from each other so as not to be affected from each other and the distance between the electron-optical apparatus 3 and the light microscope 4 is known.

The sample chamber 8 has a sample stand 30, an X stage 31, a Y stage 32, and a high-voltage power supply 36. In the present embodiment, the sample 9 is a semiconductor wafer. A negative voltage is applied to the sample 9 by the high-voltage power supply 36. By adjusting the voltage from the high-voltage power supply 36, the electron beam 19 irradiated on the sample 9 can be decelerated. Thus, irradiation energy of the electron beam to the sample 9 can be adjusted to an optimal value without changing the potential of the electron gun 10.

The X stage 31 or the Y stage 32 can reciprocatingly move the sample 9 between the electron-optical apparatus 3 and the light microscope 4.

The SEM inspection system 1 further includes an image processing part 5, a control part 6, a secondary electron detector 7, a position monitor dimension measuring device 34, a sample height measuring device 35, a correction control circuit 43, a scan signal generator 44, and an objective lens power supply 45.

The image processing part 5 includes a first image memory part 46, a second image memory part 47, a difference image calculation part 48, a defect judgment part 49, and a monitor 50. Operation instructions and operation conditions of each part of the image processing part 5 are inputted into/outputted from the control part 6.

The secondary electron detector 7 has a preamplifier 21, an AD converter 22, a light conversion means 23, an optical transmission means 24, an electrical transducing means 25, a high-voltage power supply 26, a preamplifier driving power supply 27, an AD converter driving power supply 28, and a reverse bias power supply 29. The secondary electron detector 20, the preamplifier 21, the AD converter 22, the light conversion means 23, the preamplifier driving power supply 27, and the AD converter driving power supply 28 float at positive potentials due to the high-voltage power supply 26. The secondary electron detector 20 generates an attracting electric field by the positive potentials.

The position monitor dimension measuring device 34 monitors the positions of the X stage 31 and the Y stage 32 in real time and transmits position information thereof to the control part 6 via the correction control circuit 43. The sample height measuring device 35 measures the height of the sample 9 in real time and transmits measured information to the control part 6 via the correction control circuit 43. In the present embodiment, the sample height measuring device 35 irradiates the sample 9 through a transparent window with an elongated white light after being passed through a slit, and detects the position of a reflected light by a position detection monitor to calculate the amount of change of the height from position changes.

The control part 6 generates a correction signal based on data inputted via the correction control circuit 43 and outputs the correction signal to the correction control circuit 43. The correction control circuit 43 transmits a correction signal of the objective lens 16 to objective lens power supply 45 and that of the blanking deflector 13 to the scan signal generator 44. The irradiation position of the electron beam 19 is thereby controlled. The control part 6 records the area where an electron beam has been irradiated with for each sample, even if the sample 9 is replaced.

The control part 6 has conditions such as the acceleration voltage at the time of electron beam generation, electron beam deflection width, deflection speed, timing for loading a signal of the secondary electron detector 20, and movement speed of the sample stand 30 inputted thereto in advance so that these conditions can optionally or selectively be set depending on the purpose.

Next, the procedure for inspecting the sample, or semiconductor wafers by the SEM inspection system 1 in the present embodiment will be described. The sample 9 is loaded into a sample replacement chamber (not shown). The sample 9 is mounted onto a sample holder (not shown) to be held and fixed and then, the sample replacement chamber is evacuated. When the sample replacement chamber reaches some degree of vacuum, the sample 9 is moved into the inspection chamber 2. In the inspection chamber 2, the sample 9 is put on the sample stand 30 via the X stage 31 and the Y stage 32 together with the sample holder to be held and fixed there. Pre-registered irradiation conditions for an electron beam are set and calibrations such as focusing are performed.

First, preparations are made with the light microscope 4. The sample 9 is placed at a predetermined position below the light microscope 4 by movement of the X stage 31 and the Y stage 32 in X and Y directions respectively, and an image of the light microscope of a circuit pattern formed on the sample 9 is observed with the CCD camera 42. Positions of chips where the circuit pattern is present, distances between chips, or repeat pitches and the like of a repeat pattern like memory cells are measured, and measured values are inputted into the control part 6. Also, chips to be inspected and areas to be inspected in the chip are specified, which are inputted into the control part 6. Images of a light microscope can be observed at relatively low magnification and, if the surface of the sample 9 is covered with, for example, a silicon oxide film, the sample can be observed transparently up to the substrate, and chip arrangement and layout of circuit patterns in a chip can easily be observed, so that areas to be inspected can easily be set.

When preparations such as predetermined correction work and inspection area settings by use of the light microscope 4 are completed as described above, the X stage 31 and the Y stage 32 move so as to move the sample 9 below the electron-optical apparatus 3. After the sample 9 is placed below the electron-optical apparatus 3, work similar to the correction work and inspection area settings done with the light microscope 4 is done with the electron-optical apparatus 3. Since simple inspection position checking, alignment, and position adjustments have been done based on a light microscope image and also rotation corrections have been made in advance, major adjustments are not needed.

By applying a voltage between the electron gun 10 and the extractor electrode 11, the electron beam 19 is drawn out of the electron gun 10. The electron beam 19 is irradiated with on the sample 9 by passing through the condensing lens 12, the aperture 14, the scan deflector 15, and the objective lens 16. On the basis of coordinate values stored and corrected by alignment based on a light microscope image, a scan of the electron beam 19 is performed two-dimensionally in the X and Y directions by the scan deflector 15 to the same circuit pattern as observed with the light microscope 4.

When the sample 9 is irradiated with the electron beam 19, secondary electrons 51 are generated from the sample 9. The secondary electrons 51 illuminate the reflector 17 after the trajectory thereof is bent by the ExB deflector 18, to generate second secondary electrons 52 having energy of several eV to 50 eV. The secondary electrons 52 are attracted by an attracting electric field generated by the secondary electron detector 20 before being detected by the secondary electron detector 20. Here, secondary electrons from the sample are described, but backscattered electrons from the sample may also be used.

An analog brightness signal from the secondary electron detector 20 is amplified by the preamplifier 21 of the secondary electron detector 7 before being converted into a digital signal by the AD converter 22. The digital brightness signal is sent from the light conversion means 23 to the electrical transducing means 25 of the image processing part 5 by means of the optical transmission means 24 such as an optical fiber.

The electrical transducing means 25 of the image processing part 5 converts an image signal inputted via the optical transmission means 24 again into an electric signal. Images from the electrical transducing means 25 are cut out and stored alternately in the two image memory parts 46 and 47. The difference image calculation part 48 compares images in the two image memory parts 46 and 47 to generate a difference image. The defect judgment part 49 judges whether there is any defect and if any, the type of defect on the basis of the difference image. The monitor 50 displays defect positions, types of defect, the number of defects and the like.

A requirement of the SEM inspection system in the present embodiment is a fast inspection speed. Therefore, a scan of an electron beam of an electron beam current on the order of pA at a low speed like a common conventional scanning electron microscope (SEM) is not performed, and a multiplicity of scans and superposition of their images are not performed. Moreover, an electron beam scan should be performed at high speed once or at most several times and should not be performed many times also so as to suppress charging of insulating materials. Thus, in the present embodiment, an image is obtained by performing only once a scan of an electron beam of a large current, for example, 100 nA, which is about 1000 times or more a current in a conventional scanning electron microscope.

A diffused supply type thermal field-emission electron source is used in the electron gun 10. By using the electron gun 10, a more stable electron beam current can be secured compared with, for example, a conventional tungsten/filament electron gun and a cold field-emission electron source. Thus, an electron beam image with fewer fluctuations in brightness can be obtained. Moreover, the electron beam current can be set larger with the electron gun 10 and therefore, high-speed inspection described later can be carried out.

Figure 2:
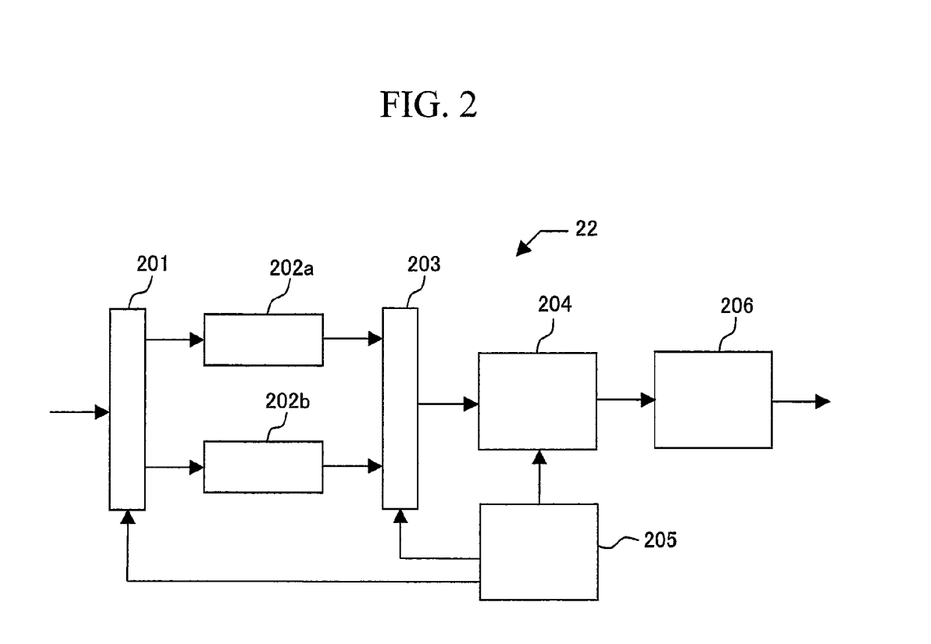
FIG. 2 is a diagram illustrating an exemplary configuration of an AD converter of a secondary electron detector in the SEM inspection system of the present invention.

An exemplary configuration of the AD converter 22 in the secondary electron detector 7 of the SEM inspection system according to the present invention will be described with reference to FIG. 2. The AD converter 22 in the present embodiment has a first analog switch 201, first and second filter circuits 202*a* and 202*b*, a second analog switch 203, an AD converter 204, a clock generator 205, and a digital signal processing circuit 206.

The two analog switches 201 and 203 enable one of the two filter circuits 202*a* and 202*b*. In the present embodiment, the first filter circuit 202*a* is used for a low sampling rate, and the second filter circuit 202*b* is used for a high sampling rate. The sampling rate is determined by the frequency of a clock signal from the clock generator 205. Here, two filter circuits are provided, but more filter circuits may be provided.

Figure 1:
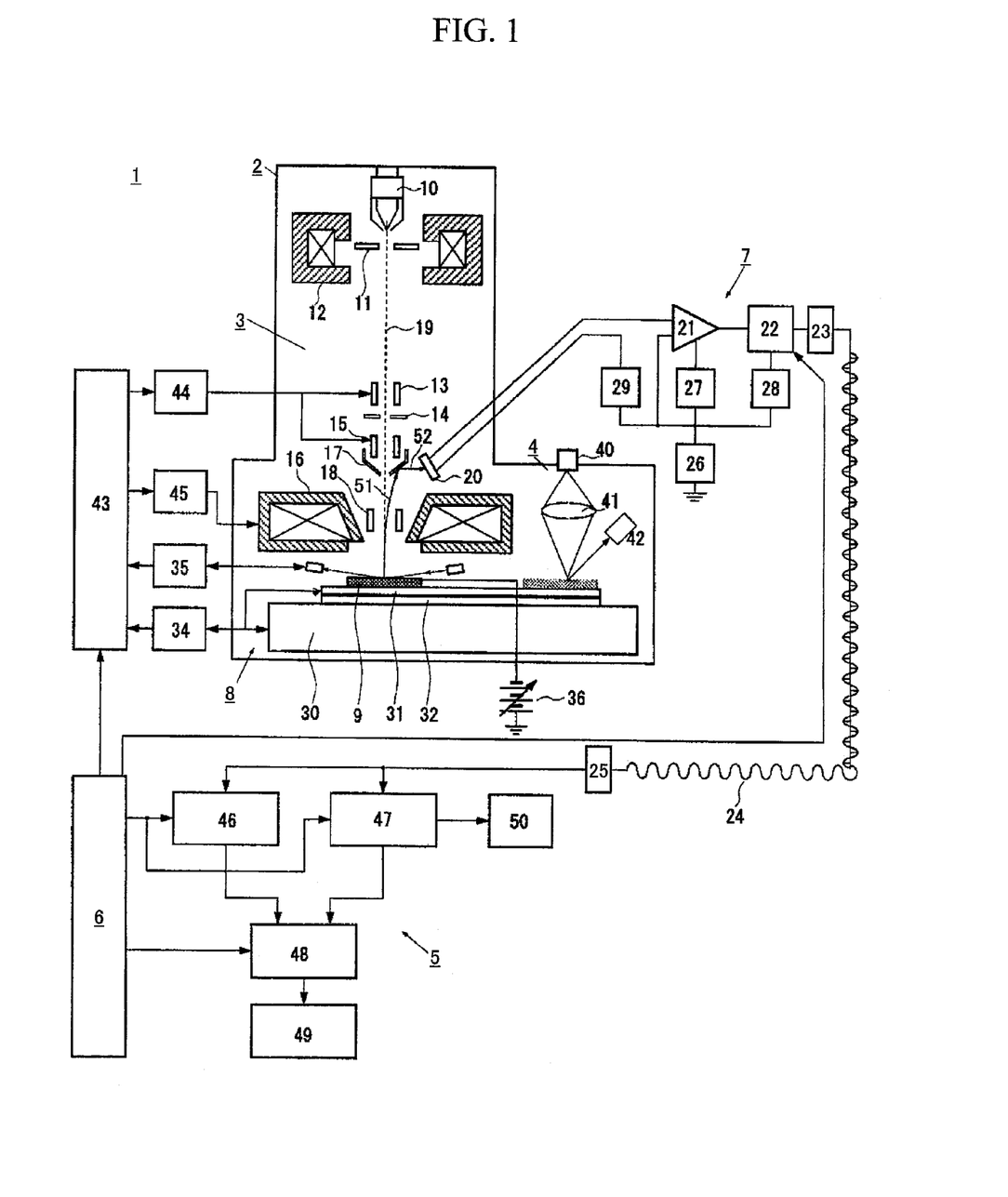
FIG. 1 is a diagram illustrating a configuration of an SEM inspection system of the present invention.

As shown in FIG. 1, an analog brightness signal from the secondary electron detector 20 is amplified by the preamplifier 21 before being supplied to the AD converter 22. The amplified analog brightness signal is smoothed by one of the filter circuits 202*a* and 202*b* before being sent to the AD converter element 204. The AD converter element 204 samples the analog brightness signal in synchronization with a clock signal of the clock generator 205 to generate digital signal. That is, sampling is performed at the same sampling rate as the frequency of the clock signal.

The digital signal processing circuit 206 performs addition processing and average processing of a digital signal. Addition processing and average processing will be described below with reference to FIG. 4. As shown in FIG. 1, a digital signal from the digital signal processing circuit 206 is sent to the light conversion means 23.

Figure 3:
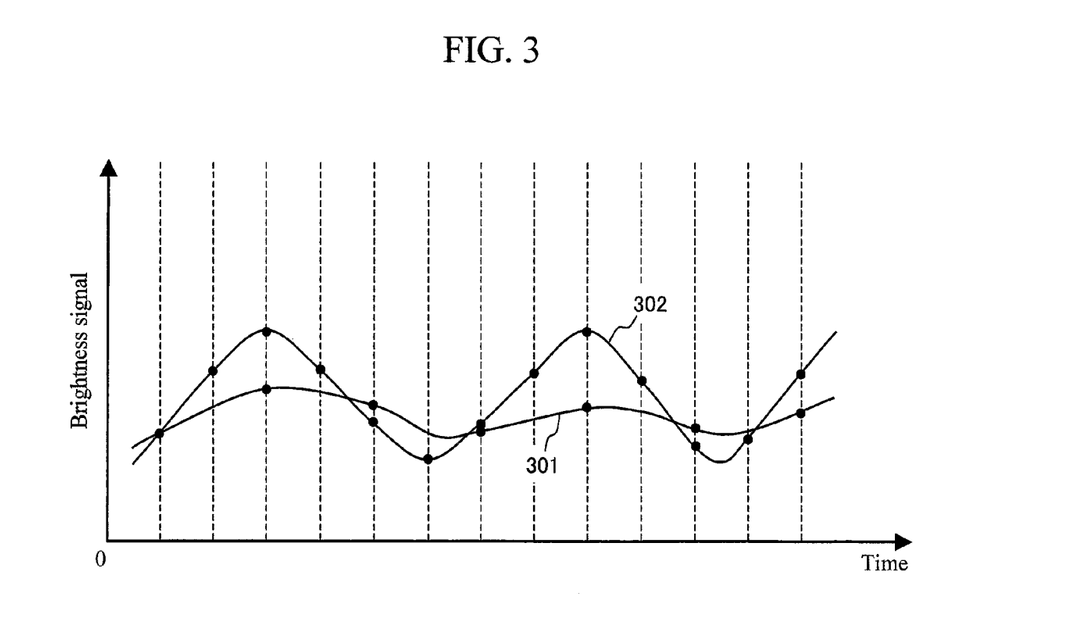
FIG. 3 is a diagram illustrating operations of two filter circuits of the AD converter of the secondary electron detector in the SEM inspection system of the present invention.

Smoothing processing by the two filter circuits 202*a* and 202*b* will be described with reference to FIG. 3. A curve 301 shows an exemplary signal after smoothing processing for the case of a low sampling rate, and a curve 302 shows an exemplary signal after smoothing processing for the case of a high sampling rate. Black circles on the curves 301 and 302 indicate sampling times. As shown by the curve 301, smoothing processing is performed for the case of a low sampling rate so that fluctuations become smaller. Therefore, the first filter circuit 202*a* has a function to smooth fluctuations to make them smaller like the curve 301. On the other hand, as shown by the curve 302, relatively large fluctuations remain even after smoothing for the case of a high sampling rate. Therefore, the second filter circuit 202*b* has a function to smooth fluctuations while retaining relatively large fluctuations like the curve 302.

Figure 4A:
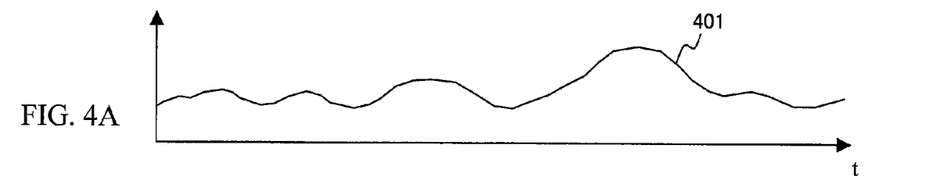
FIG. 4A-FIG. 4F are diagrams illustrating exemplary addition processing and average processing in a digital signal processing circuit of the secondary electron detector in the SEM inspection system of the present invention.
Figure 4B:
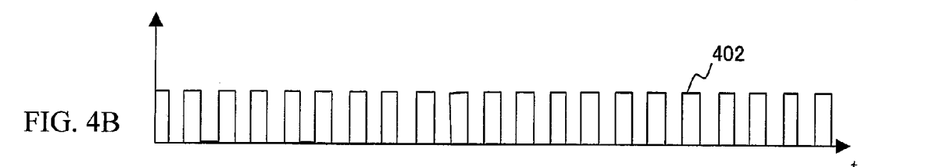
Figure 4C:
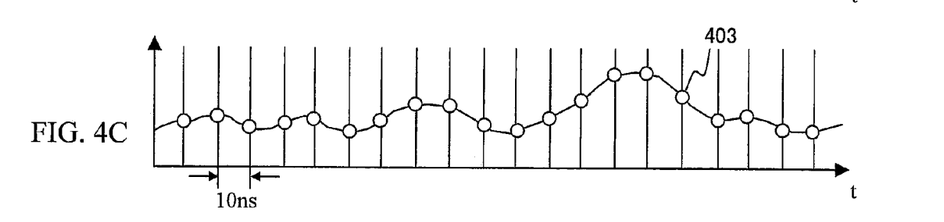

Exemplary addition processing and average processing in the digital signal processing circuit 206 will be described with reference to FIG. 4A-FIG. 4F. FIG. 4A shows temporal changes of strength of an analog signal 401 supplied to the AD converter 22. The horizontal axis is a time axis. The analog signal 401 represents the level of output signal of the secondary electron detector 20. FIG. 4B shows a clock signal 402 of the clock generator 205. The frequency of the clock signal 402 represents the sampling frequency, that is, the sampling rate. FIG. 4C shows a state in which the analog signal 401 is sampled when the clock signal 402 rises. This processing is performed by the AD converter element 204. Vertical lines at regular intervals in FIG. 4C represent rises of the clock signals 402 and circles on the vertical lines represent sampled signals 403.

Addition processing and average processing of the sampled signals 403 obtained in this manner by the AD converter element 204 are performed by the digital signal processing circuit 206, as described below.

Figure 4D:
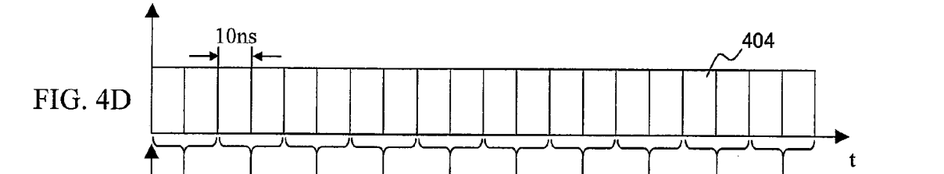

FIG. 4D shows a state in which the sampled signal 403 is digitized. A rectangle 404 on the horizontal axis is formed each time the clock signal 402 rises. A digital value of the sampled signal 403 is stored in each of the rectangles 404. Here, 8-bit digital values are used. Therefore, a number ranging from 0 to 255 is stored in each of the rectangles 404 in FIG. 4D.

Figure 4E:
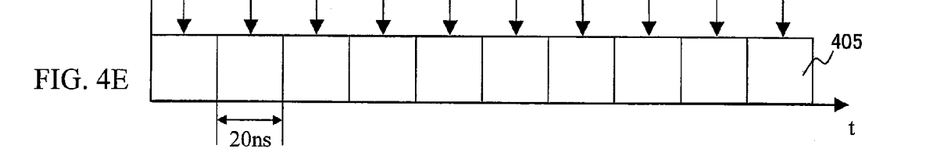

FIG. 4E shows addition processing by the digital signal processing circuit 206. In the addition processing, 8-bit digital values in FIG. 4D are added on a two by two adjacent rectangle basis. A rectangle 405 on the horizontal axis is formed for every couple of pulses of the clock signal 402. A sum of digital values of two adjacent rectangles in FIG. 4D is stored in each of the rectangles 405. Addition of 8-bit digital values produces a 9-bit digital value. Therefore, a number ranging from 0 to 510 is stored in each of the rectangles 405 in FIG. 4E.

Figure 4F:
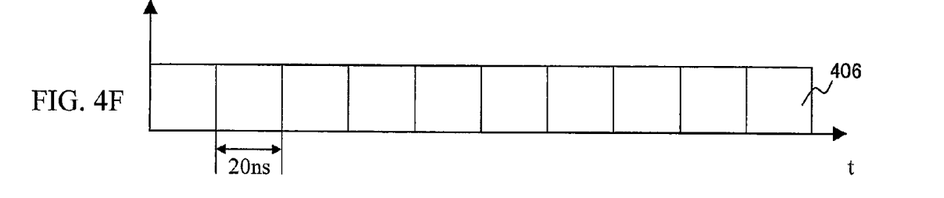

FIG. 4F shows average processing by the digital signal processing circuit 206. In the average processing, 9-bit digital values in FIG. 4E are divided by 2. A rectangle 406 on the horizontal axis is formed for every couple of pulses of the clock signal 402. A number half the digital value in each of the rectangles 405 in FIG. 4E is stored in each of the rectangles 406. A fraction less than 1 is discarded. Division of a 9-bit digital value by 2 produces an 8-bit digital value. Therefore, a number ranging from 0 to 255 is stored in each of the rectangles 406 in FIG. 4F. A digital value ranging from 0 to 255 stored in each of the rectangles 406 in FIG. 4F forms one pixel data. Using these digital values, a pixel signal is generated.

Comparison of FIG. 4D and FIG. 4F shows that the frequency of a digital signal after addition processing and average processing shown in FIG. 4F is half the sampling rate in FIG. 4D. If, for example, the frequency of the clock signal 402 in FIG. 4B is 100 MHz, the frequency of a digital signal after addition processing and average processing in FIG. 4F will be 50 MHz. Therefore, the sampling rate of an output signal from the secondary electron detector 20 is substantially halved by addition processing and average processing.

Generally, as the sampling rate decreases, the storage time of secondary electrons in the secondary electron detector 20 becomes longer and brightness signal strength increases. If the sampling rate is high, the storage time of secondary electrons in the secondary electron detector 20 becomes shorter and brightness signal strength decreases. In the present embodiment, a digital signal whose frequency is 50 MHz can be obtained by using the clock signal 402 whose frequency is 100 MHz. Therefore, this is substantially like the sampling rate being halved, and contrast of a brightness signal is enhanced, making an image sharper.

Figure 5:
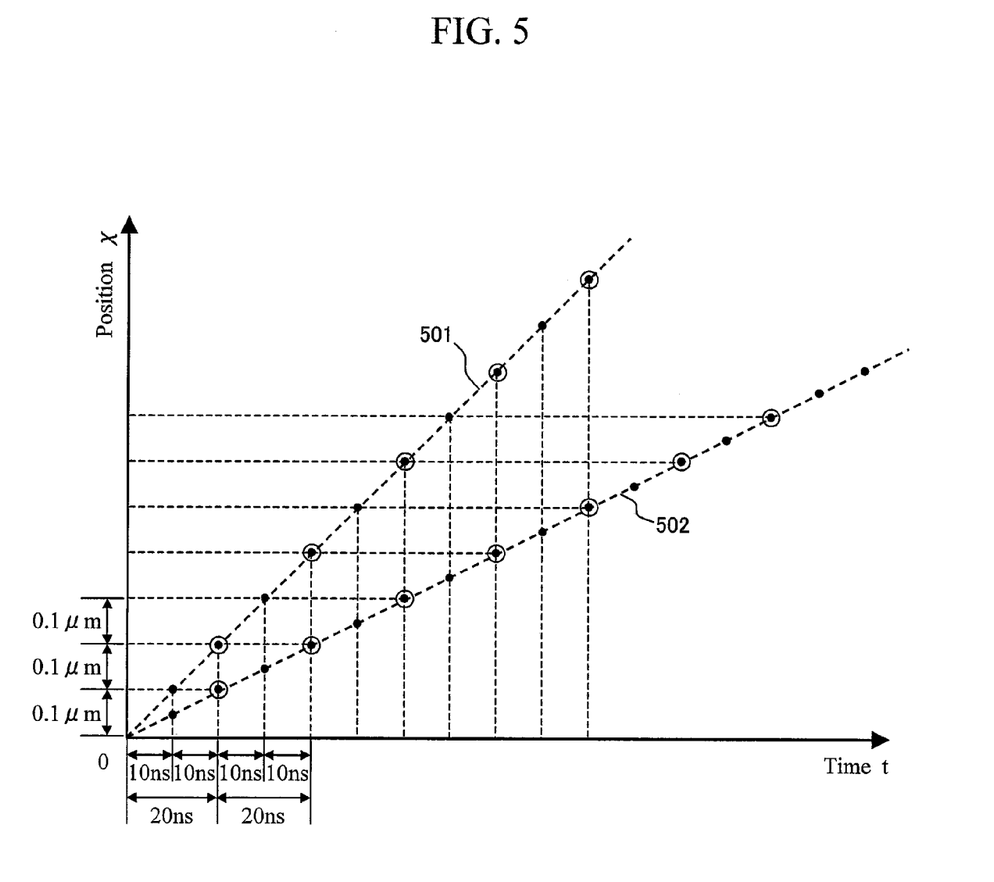
FIG. 5 is a diagram illustrating a relationship between a scanning speed and a sampling rate in the SEM inspection system of the present invention.

A relationship between the scanning speed and sampling rate will be described with reference to FIG. 5. FIG. 5 shows a relationship between the sampling time and sampling position when an output signal of the secondary electron detector 20 is sampled using the clock signal 402 whose frequency is 100 MHz. The vertical axis shows the scanning position on the sample surface and the horizontal axis shows the time. In the present embodiment, the sampling rate is 100 MHz and sampling is performed every 10 ns. A straight line 501 is a case when the scanning speed of an electron beam is 10 m/s and a straight line 502 is a case when the scanning speed of an electron beam is 5 m/s. Points (indicated by black circles) on the straight lines 501 and 502 indicate sampling points.

For the straight line 501, sampling is performed on the sample surface every 0.1 μm, and for the straight line 502, sampling is performed on the sample surface every 0.05 μm.

Digital values indicated by double circles on the straight lines 501 and 502 are obtained by both adding digital values at two adjacent sampling points on the straight lines 501 and 502 and taking an average thereof. The frequency of these digital values after the addition and average processing is 50 MHz. According to the present invention, one pixel data is generated using one digital value. In the present embodiment, frequencies of digital signals indicated by double circles are half sampling rates indicated by black circles. Therefore, according to the present invention, this is substantially like the sampling rate being halved, leading to sharper images with enhanced contrast.

For the straight line 501, digital values indicated by double circles are obtained every 0.2 μm on the sample surface. For the straight line 502, on the other hand, digital values indicated by double circles are obtained every 0.1 μm on the sample surface. Comparison of the straight line 501 and the straight line 502 shows that, even if the sampling rate is the same, the interval of sampling positions on the sample surface becomes shorter if the scanning speed is made slower. Therefore, sharper images with enhanced contrast can be obtained by making the scanning speed slower.

Figure 6:
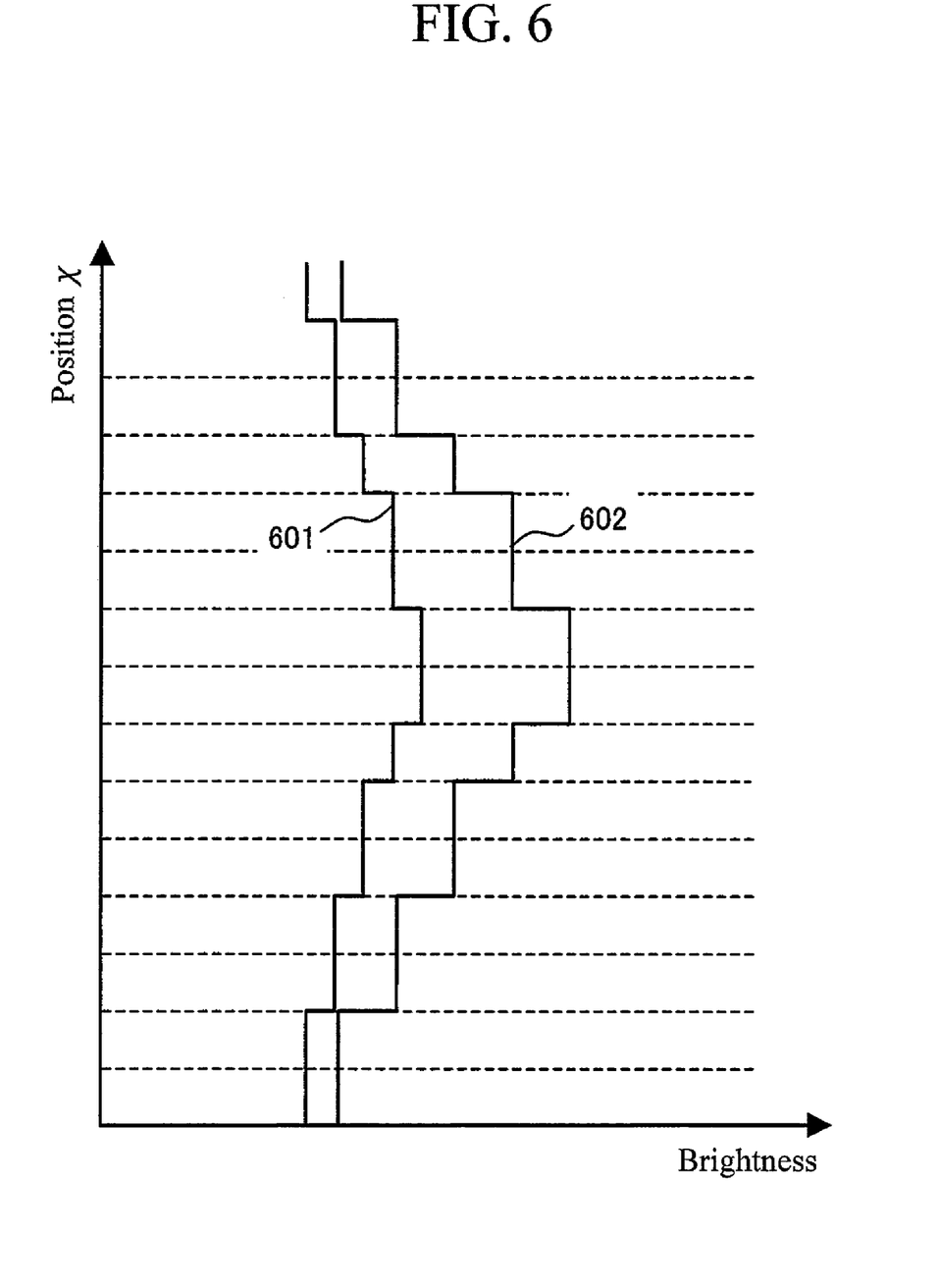
FIG. 6 is a diagram illustrating contrast of a brightness signal in the SEM inspection system of the present invention.

Results of addition processing and average processing according to the present invention will be described with reference to FIG. 6. The vertical axis in FIG. 6 shows the scanning position on the sample surface and the horizontal axis shows brightness. A polygonal line 601 shows a brightness signal obtained according to a conventional method. That is, neither addition processing nor average processing is performed. A polygonal line 602 shows a digital signal after performing addition processing and average processing according to the present invention. As is evident from FIG. 6, the brightness signal obtained according to the present invention has enhanced contrast compared with that obtained according to a conventional method.

Figure 7A:
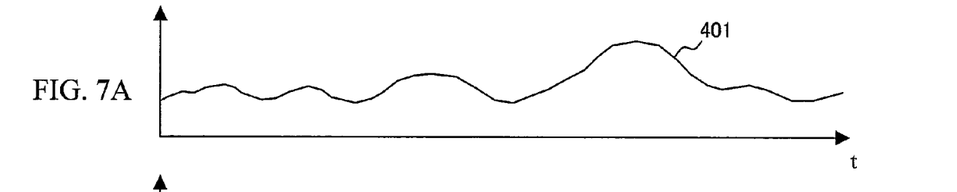
FIG. 7A-FIG. 7G are diagrams illustrating other exemplary addition processing and average processing in the digital signal processing circuit of the secondary electron detector in the SEM inspection system of the present invention.
Figure 7B:
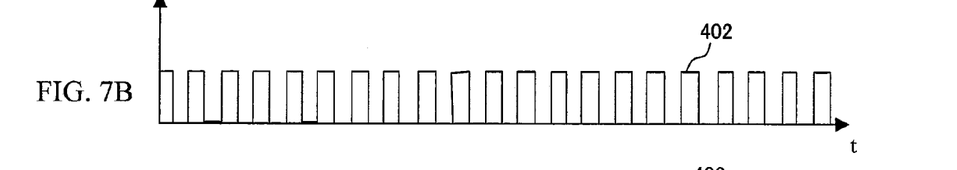
Figure 7C:
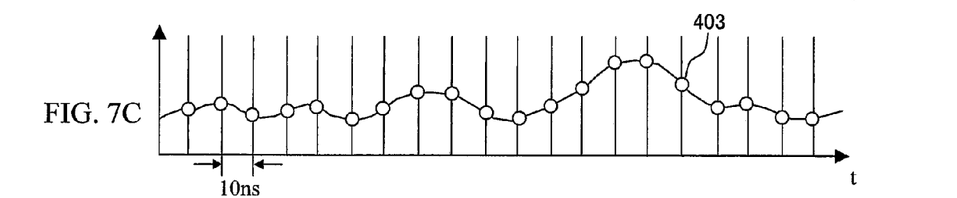

Other exemplary addition processing and average processing in the digital signal processing circuit 206 will be described with reference to FIG. 7A-FIG. 7G. Processing from FIG. 7A to FIG. 7E is the same as that from FIG. 4A to FIG. 4E. FIG. 7A shows temporal changes of strength of the analog signal 401 supplied to the AD converter 22. FIG. 7B shows the clock signal 402 of the clock generator 205. FIG. 7C shows a state in which the analog signal 401 is sampled when the clock signal 402 rises.

Figures 7D, 7E:
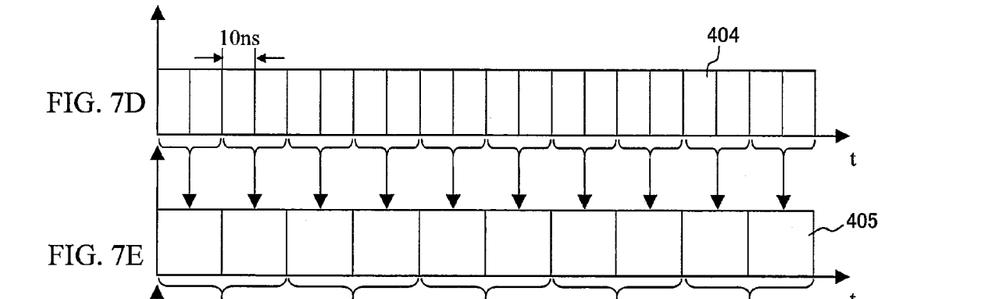

FIG. 7D shows a state in which the sampled signal 403 is digitized. The rectangle 404 on the horizontal axis is formed each time the clock signal 402 rises. An 8-bit digital value, that is, a number ranging from 0 to 255 is stored in each of the rectangles 404.

FIG. 7E shows first addition processing by the digital signal processing circuit 206. The rectangle 405 on the horizontal axis is formed for every couple of pulses of the clock signal 402. A 9-bit digital value, that is, a number ranging from 0 to 511 is stored in each of the rectangles 405.

Figure 7F:
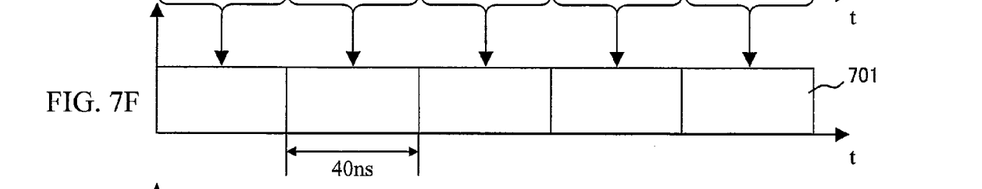

FIG. 7F shows second addition processing by the digital signal processing circuit 206. In the second addition processing, 9-bit digital values in FIG. 7E are added on a two by two adjacent rectangle basis. A rectangle 701 on the horizontal axis is formed for every set of four pulses of the clock signal 402. A sum of digital values of two adjacent rectangles in FIG. 7E is stored in each of the rectangles 701. Addition of 9-bit digital values produces a 10-bit digital value. Therefore, a number ranging from 0 to 1023 is stored in each of the rectangles 701 in FIG. 7F.

Figure 7G:
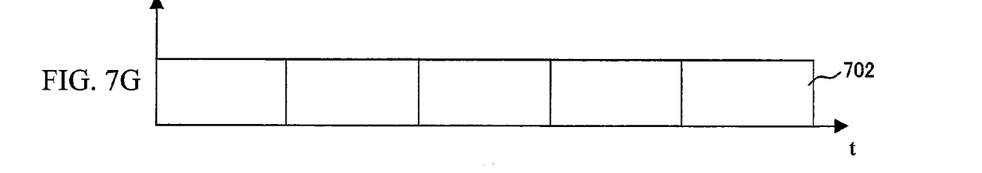

FIG. 7G shows average processing by the digital signal processing circuit 206. In the average processing, 10-bit digital values in FIG. 7F are divided by 4. A rectangle 702 on the horizontal axis is formed for every set of four pulses of the clock signal 402. A number equal to one fourth of the digital value held in each of the rectangles 701 in FIG. 7F is stored in each of the rectangles 702. A fraction less than 1 is discarded. Division of a 10-bit digital value by 4 produces an 8-bit digital value. Therefore, a number ranging from 0 to 255 is stored in each of the rectangles 702 in FIG. 7G. A digital value ranging from 0 to 255 stored in each of the rectangles 702 in FIG. 7G forms one pixel data. Using these digital values, a pixel signal is generated.

Here, a 10-bit digital value in FIG. 7F is divided, for example, by 2. The rectangle 702 on the horizontal axis is formed for every set of four pulses of the clock signal 402. A number half the digital value held in each of the rectangles 701 in FIG. 7F is stored in the rectangle 702. A fraction less than 1 is discarded. Division of a 10-bit digital value by 2 produces a 9-bit digital value. Therefore, a number ranging from 0 to 511 is stored in each of the rectangles 702 in FIG. 7G. A digital value ranging from 0 to 511 stored in each of the rectangles 702 in FIG. 7G forms one pixel data. Using these digital values, a pixel signal having the number of bits larger than that of the sampled signal can be generated, leading to improved resolution.

Figure 8A:
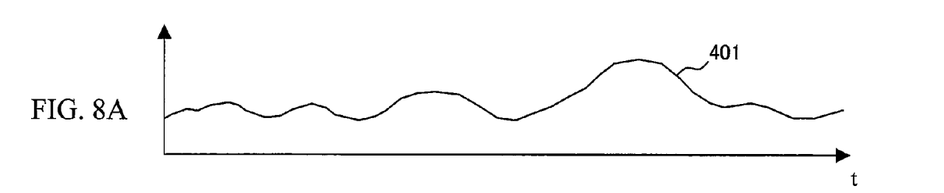
FIG. 8A-FIG. 8F are diagrams illustrating still other exemplary addition processing and average processing in the digital signal processing circuit of the secondary electron detector in the SEM inspection system of the present invention.
Figure 8B:
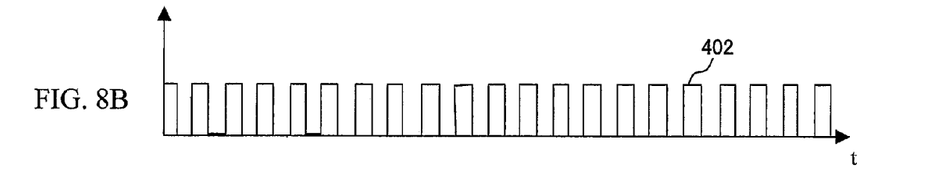
Figure 8C:
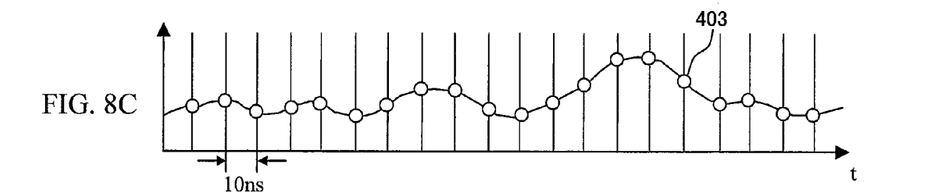
Figure 8D:
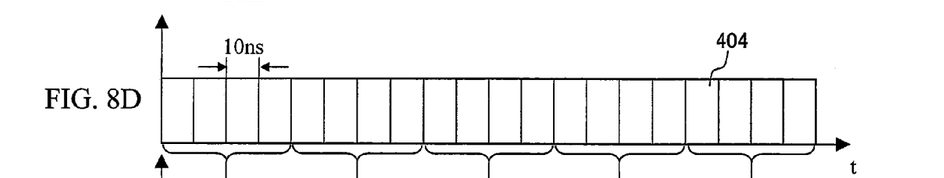

Still other exemplary addition processing and average processing in the digital signal processing circuit 206 will be described with reference to FIG. 8A-FIG. 8F. Processing from FIG. 8A to FIG. 8D is the same as that from FIG. 4A to FIG. 4D. That is, FIG. 8A shows temporal changes of strength of the analog signal 401 supplied to the AD converter 22. FIG. 8B shows the clock signal 402 of the clock generator 205. FIG. 8C shows a state in which the analog signal 401 is sampled when the clock signal 402 rises. FIG. 8D shows a state in which the sampled signal 403 is digitized. An 8-bit digital value of the sampled signal 403, that is, a number ranging from 0 to 255 is stored in each of the rectangles 404 on the horizontal axis.

Figure 8E:
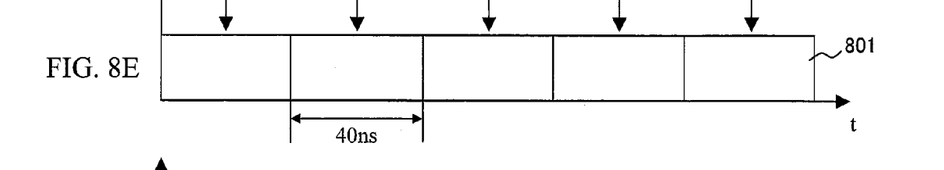

FIG. 8E shows addition processing by the digital signal processing circuit 206. In the addition processing of the present embodiment, 8-bit digital values in FIG. 8D are added on a four by four adjacent rectangle basis. A rectangle 801 on the horizontal axis is formed for every set of four pulses of the clock signal 402. A sum of digital values of four adjacent rectangles in FIG. 8D is stored in each of the rectangles 801. Addition of four 8-bit digital values produces a 10-bit digital value. Therefore, a number ranging from 0 to 1023 is stored in each of the rectangles 801 in FIG. 8E.

Figure 8F:
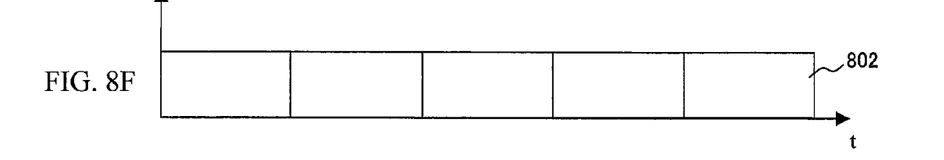

FIG. 8F shows average processing by the digital signal processing circuit 206. In the average processing, 10-bit digital values in FIG. 8E are divided by 4. A rectangle 802 on the horizontal axis is formed for every set of four pulses of the clock signal 402. A number equal to one fourth of the digital value held in each of the rectangles 801 in FIG. 8E is stored in each of the rectangles 802. A fraction less than 1 is discarded. Division of a 10-bit digital value by 4 produces an 8-bit digital value. Therefore, a number ranging from 0 to 255 is stored in each of the rectangles 802 in FIG. 8F. A digital value ranging from 0 to 255 stored in each of the rectangles 802 in FIG. 8F forms one pixel data. Using these digital values, a pixel signal is generated.

Here, a 10-bit digital value in FIG. 8E is divided, for example, by 2. The rectangle 802 on the horizontal axis is formed for every set of four pulses of the clock signal 402. A number half the digital value held in each of the rectangles 801 in FIG. 8E is stored in the rectangle 802. A fraction less than 1 is discarded. Division of a 10-bit digital value by 2 produces a 9-bit digital value. Therefore, a number ranging from 0 to 511 is stored in each of the rectangles 802 in FIG. 8F A digital value ranging from 0 to 511 stored in each of the rectangles 802 in FIG. 8F forms one pixel data. Using these digital values, a pixel signal having the number of bits larger than that of the sampled signal can be generated, leading to improved resolution.

In the example, in FIG. 4, the sampling rate is 100 MHz, and the frequency of a digital signal after addition and average processing is 50 MHz. Therefore, each digital value of the digital signal after the addition and average processing shown in FIG. 4F corresponds to two digital values of the sampled signal shown in FIG. 4D. That is, one pixel data corresponds to couple of sampled signal data.

The period of a digital signal after addition and average processing is 20 ns. Therefore, each digital value of the digital signal after the addition and average processing corresponds to a storage amount of a brightness signal during a time of 20 ns. That is, one pixel data corresponds to the storage amount of a brightness signal during a time of 20 ns.

Moreover, it is preferable that the storage amount of a brightness signal corresponding to one pixel data be always the same even if the sampling rate changes. For this purpose, a condition of the period of a digital signal after addition and average processing being constant is sufficient. If the sampling rate is f and the sampling period is T, the period Te of a digital signal after addition and average processing can be obtained from the following formula:

$$Te = T \times N = (1/f) \times (f/fe) = 1/fe$$

where N is the ratio of the sampling rate f to the frequency fe of a digital signal after addition and average processing. N represents the number of sampled signal data per pixel. Te represents the storage amount of a brightness signal per pixel. fe is the frequency of a digital signal after addition and average processing. In the example in FIG. 4, the period Te of a digital signal after addition and average processing is $10 \times 2 = 20$ ns. The number of sampled signal data per pixel is 2. In the examples in FIG. 7 and FIG. 8, the frequency of a digital signal after addition and average processing is 25 MHz and the number of sampled signal data per pixel is 4. Therefore, the period Te of a digital signal after addition and average processing is $10 \times 4 = 40$ ns.

Figure 9:
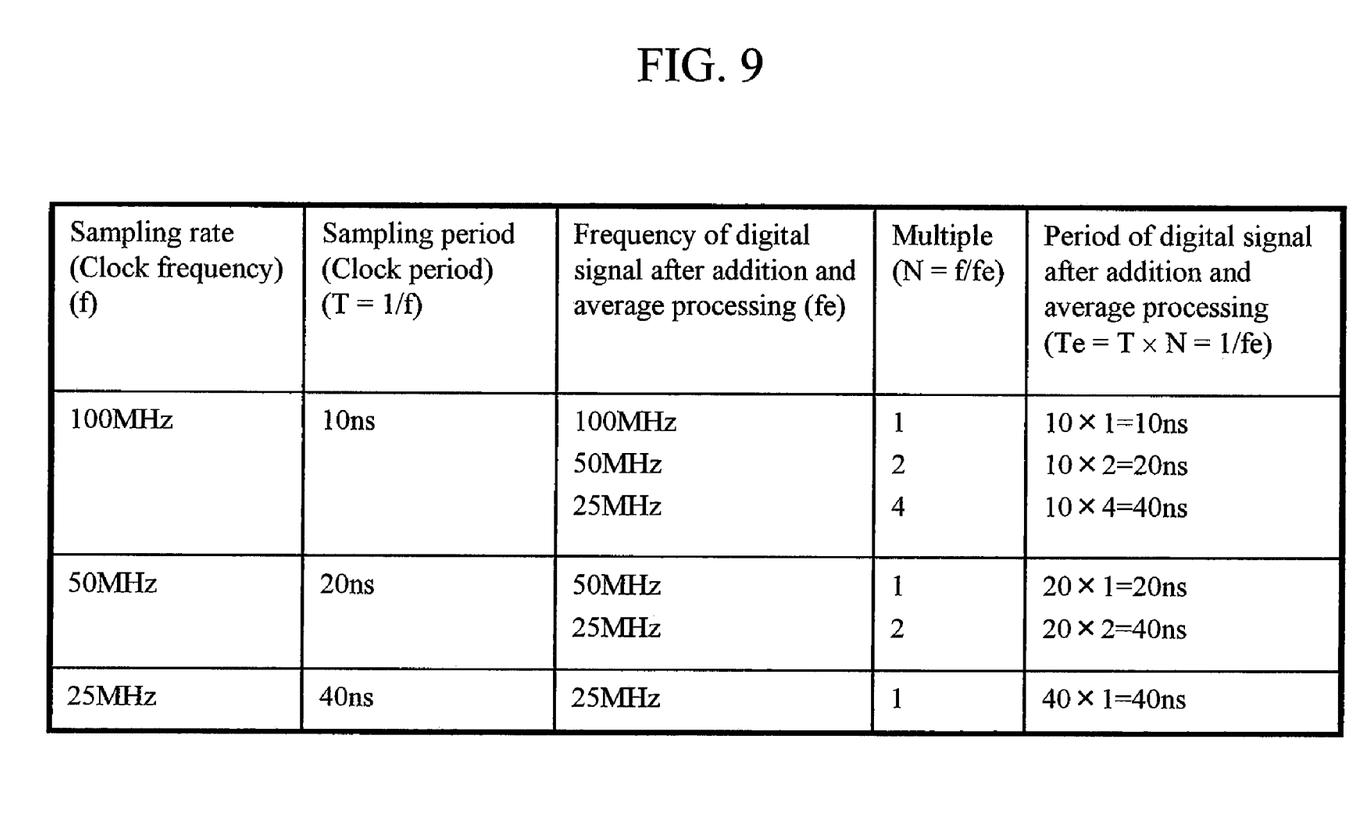
FIG. 9 is a diagram showing the relationship between clock frequencies and digital signal periods after addition and average processing in the SEM inspection system of the present invention.

FIG. 9 shows calculation results of the period Te ($=T \times N$) of a digital signal after addition and average processing when the sampling rate (clock frequency) and the frequency of a digital signal after addition and average processing are given. First, a case in which the period Te of a digital signal after addition and average processing is set to 20 ns is considered. The period Te of a digital signal after addition and average processing becomes 20 ns in two cases: when the sampling rate is 100 MHz and the frequency of a digital signal after addition and average processing is 50 MHz and when the sampling rate is 50 MHz and the frequency of a digital signal after addition and average processing is 50 MHz. However, the sampling rate f and the frequency fe of a digital signal after addition and average processing are the same in the latter case. This is a case of a conventional technology in which addition processing and average processing are not performed.

Next, a case in which the period Te of a digital signal after addition and average processing is set to 40 ns is considered. The period Te of a digital signal after addition and average processing becomes 40 ns in three cases: when the sampling rate is 100 MHz and the frequency of a digital signal after addition and average processing is 25 MHz, when the sampling rate is 50 MHz and the frequency of a digital signal after addition and average processing is 25 MHz, and when the sampling rate is 25 MHz and the frequency of a digital signal after addition and average processing is 25 MHz. In the last case of these cases, the sampling rate f and the frequency fe of a digital signal after addition and average processing are the same. This is a case of a conventional technology in which addition processing and average processing are not performed.

Figure 10:
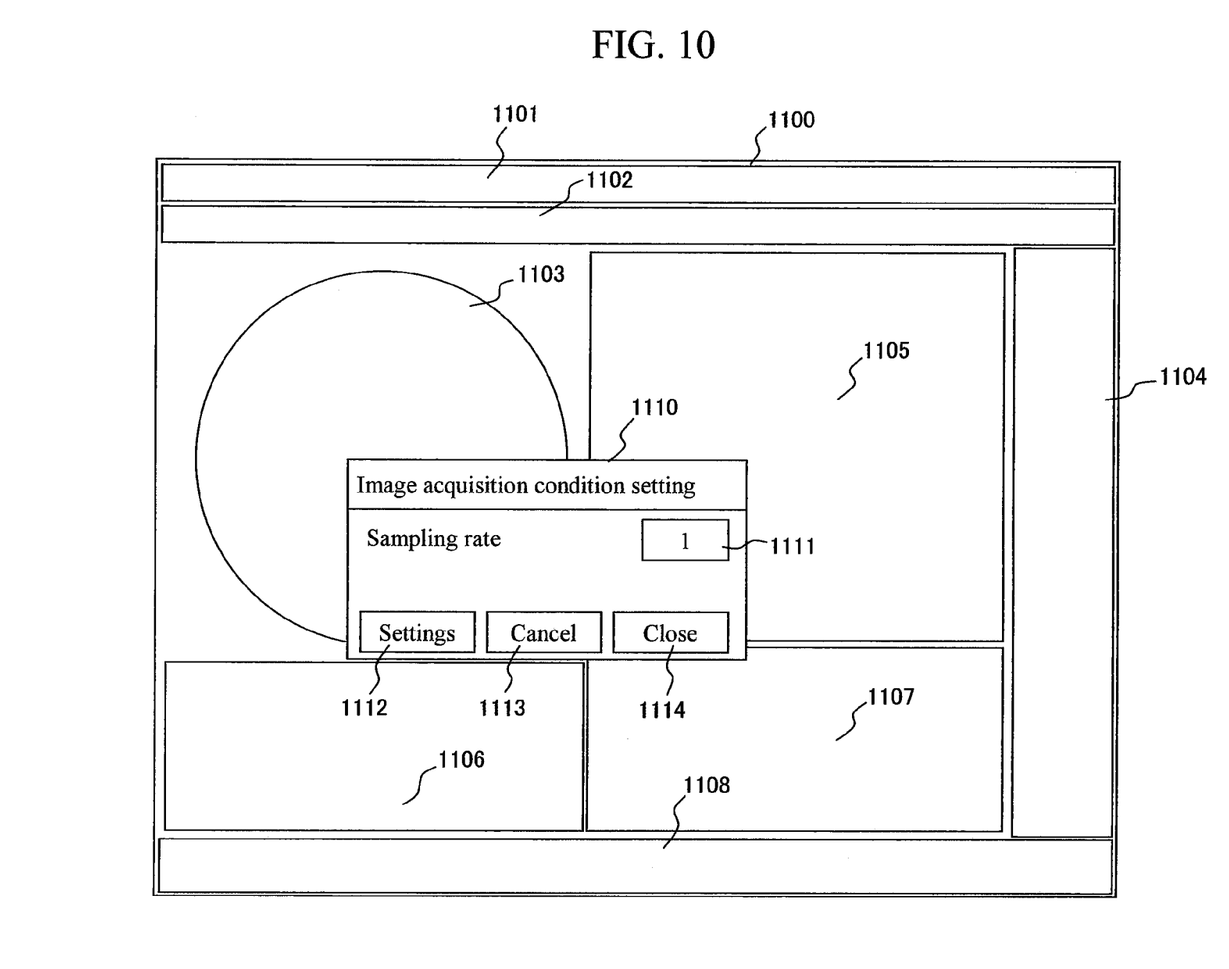
FIG. 10 is a diagram showing an exemplary input screen of a monitor in the SEM inspection system of the present invention.

FIG. 10 shows an exemplary input screen of the monitor 50. An input screen 1100 in the present embodiment has a message area 1101, an input prompting message area 1102, a map display area 1103, a common button area 1104, information display areas 1105, 1106, and 1107, and a menu selection button area 1108. These areas are laid out in various ways and the layout thereof is not limited to the example shown in FIG. 10. For example, if a button arranged in the common button area 1104 is clicked, an image acquisition condition setting window 1110 is displayed in the input screen 1100. The image acquisition condition setting window 1110 has an input field 1111 where the sampling rate is inputted. Any sampling rate can be set in the input field 1111. For example, any sampling rate may be set, if the standard value of the sampling rate is 1, as a ratio to the standard value. The image acquisition condition setting window 1110 also has a setting button 1112, a cancel button 1113, and a close button 1114 arranged therein. If a sampling rate is inputted into the input field 1111 and the setting button 1112 is clicked, the inputted sampling rate is set. If the cancel button 1113 is clicked, a value inputted in the input field 1111 is canceled. If the close button 1114 is clicked, the image acquisition condition setting window 1110 disappears.

Embodiments of the present invention have been described, but the present invention is not limited to these embodiments and a person skilled in the art will easily understand that various modifications can be made within the scope of the invention defined by claims thereof.

Further, the present invention has the following constitution:

(1) An inspection system having a scanning electron microscope, including:
a scan deflector for performing a scan of an electron beam on a sample surface;
an objective lens for focusing the electron beam on the sample surface;
a secondary electron detector for detecting secondary electrons or backscattered electrons from the sample to generate an analog brightness signal;
an AD converter for sampling the analog brightness signal at a predetermined sampling rate; and
a digital signal processing circuit for generating an image signal from a sampled signal generated by the AD converter, wherein
the digital signal processing circuit generates a digital brightness signal of a frequency smaller than that of the sampling rate by adding contiguous digital values contained in the sampled signal on a predetermined number by predetermined number digital value basis, and divides each digital value of the generated digital brightness signals by a number smaller than the number of times of the addition to generate a digital brightness signal having the number of bits larger than that digital values of the sampled signal before generating an image signal in which each digital value of the divided digital brightness signal constitutes one pixel data.

(2) In the inspection system having a scanning electron microscope in (1), the digital signal processing circuit sets the frequency of the digital brightness signal so that a period of the digital brightness signal does not change even if the sampling rate changes.

(3) The inspection system having a scanning electron microscope in (1) further includes a first image memory part and a second image memory part for successively storing image signals from the digital signal processing circuit alternately, a difference image calculation part for calculating a difference image of images stored in the two image memory parts, and a defect judgment part for judging whether there is any defect of a wiring pattern of a semiconductor wafer, which is the sample, and if any, the type of defect, on the basis of the difference image.

(4) The inspection system having a scanning electron microscope in (1) further includes a monitor for displaying an image after an image signal from the digital signal processing circuit being inputted.

(5) An image generation method using a scanning electron microscope, including the steps of:
causing a scan deflector to perform a scan of an electron beam on a sample surface;
detecting secondary electrons or backscattered electrons from the sample by a secondary electron detector to generate an analog brightness signal;
sampling the analog brightness signal at a predetermined sampling rate by a sampling circuit; and
generating an image signal from a sampled signal generated by the sampling circuit, wherein
the step of generating the image signal generates a digital brightness signal of a frequency smaller than that of the sampling rate by adding contiguous digital values contained in the sampled signal on a predetermined number by predetermined number digital value basis, and divides each digital value of the generated digital brightness signals by a number smaller than the number of times of the addition to generate a digital brightness signal having the number of bits larger than that digital values of the sampled signal before generating an image signal in which each digital value of the divided digital brightness signal constitutes one pixel data.

(6) In the image generation method using a scanning electron microscope in (5), the step of generating the image signal sets the frequency of the digital brightness signal so that a period of the digital brightness signal does not change even if the sampling rate changes.

(7) A scanning electron microscope; including:
a scan deflector for performing a scan of an electron beam on a sample surface;
an objective lens for focusing the electron beam on the sample surface;
a secondary electron detector for detecting secondary electrons or backscattered electrons from the sample to generate an analog brightness signal;
an AD converter for sampling the analog brightness signal at a predetermined sampling rate; and
a digital signal processing circuit for generating an image signal from a sampled signal generated by the AD converter, wherein
the digital signal processing circuit generates a digital brightness signal of a frequency equal to 1/N of that of the sampling rate by adding contiguous digital values contained in the sampled signal on a N by N digital value basis and divides each added digital value of the sampled signal by N so that a number of bits of the generated digital brightness signal becomes equal to that of digital values of the sampled signal, to generate an image signal in which each digital value of the divided digital brightness signal constitutes one pixel data.

(8) In the scanning electron microscope in (7), the digital signal processing circuit sets the frequency of the digital brightness signal so that a period of the digital brightness signal does not change even if the sampling rate changes.

(9) A scanning electron microscope; including:
  a scan deflector for performing a scan of an electron beam on a sample surface;
  an objective lens for focusing the electron beam on the sample surface;
  a secondary electron detector for detecting secondary electrons or backscattered electrons from the sample to generate an analog brightness signal;
  an AD converter for sampling the analog brightness signal at a predetermined sampling rate; and
  a digital signal processing circuit for generating an image signal from a sampled signal generated by the AD converter, wherein
  the digital signal processing circuit generates a digital brightness signal of a frequency equal to 1/N of that of the sampling rate by adding contiguous digital values contained in the sampled signal on a N by N digital value basis, and divides each added digital value of the sampled signal by a number smaller than N so that the number of bits of the generated digital brightness signal becomes larger than that of digital values of the sampled signal, to generate an image signal in which each digital value of the divided digital brightness signal constitutes one pixel data.

(10) In the scanning electron microscope in (9), the digital signal processing circuit sets the frequency of the digital brightness signal so that a period of the digital brightness signal does not change even if the sampling rate changes.

(11) An inspection system having a scanning electron microscope for detecting any defect of a sample by detecting a signal generated after irradiating the sample with an electron beam, including:
  a signal processing circuit for detecting the defect by sampling the detected signal at a predetermined sampling rate to create an image, wherein
  the sampling rate can optionally be set.

(12) An inspection system having a scanning electron microscope for detecting any defect of a sample by detecting a signal generated after irradiating the sample with an electron beam, including:
  an AD converter for sampling the detected signal at a predetermined sampling rate;
  a signal processing circuit for generating an image signal from a sampled signal generated by the AD converter; and
  a defect detection circuit for detecting the defect by comparing the image signal generated by the signal processing circuit with a predetermined reference image, wherein
  the sampling rate at which the detected signal is sampled by the AD converter can optionally be set before irradiating the sample with the electron beam.

(13) An inspection system having a scanning electron microscope for detecting any defect of a sample by detecting a signal generated after irradiating the sample with an electron beam, including:
  a signal processing circuit for detecting the defect by sampling the detected signal at a predetermined sampling rate to create an image; and
  a display device for displaying an image of the defect, wherein
  an area in which the sampling rate is set is displayed in the display device.

What is claimed is:

1. An inspection system having a scanning electron microscope, comprising:
  a scan deflector for performing a scan of an electron beam on a sample surface;
  an objective lens for focusing the electron beam on the sample surface;
  a secondary electron detector for detecting secondary electrons or backscattered electrons from the sample to generate an analog brightness signal;
  an AD converter for sampling the analog brightness signal at a predetermined sampling rate; and
  a digital signal processing circuit for generating an image signal from a sampled signal generated by the AD converter, wherein
  the digital signal processing circuit generates a digital brightness signal of a frequency smaller than that of the sampling rate by adding contiguous digital values contained in the sampled signal on a predetermined number by predetermined number digital value basis, and divides each digital value of the generated digital brightness signals by a number equal to the number of times of the addition so that the number of bits of the generated digital brightness signal becomes equal to that of digital values of the sampled signal to generate an image signal in which each digital value of the divided digital brightness signal constitutes one pixel data.

2. The inspection system having a scanning electron microscope according to claim 1, wherein the digital signal processing circuit sets the frequency of the digital brightness signal so that a period of the digital brightness signal does not change even if the sampling rate changes.

3. The inspection system having a scanning electron microscope according to claim 1, further comprising:
  a first image memory part and a second image memory part for successively storing image signals from the digital signal processing circuit alternately;
  a difference image calculation part for calculating a difference image of images stored in the two image memory parts; and
  a defect judgment part for judging whether there is any defect of a wiring pattern of a semiconductor wafer, which is the sample, and if any, the type of defect, on the basis of the difference image.

4. The inspection system having a scanning electron microscope according to claim 1, further comprising: a monitor for displaying an image after an image signal from the digital signal processing circuit being inputted.

5. An image generation method using a scanning electron microscope, comprising the steps of:
  causing a scan deflector to perform a scan of an electron beam on a sample surface;
  detecting secondary electrons or backscattered electrons from the sample by a secondary electron detector to generate an analog brightness signal;
  sampling the analog brightness signal at a predetermined sampling rate by a sampling circuit; and
  generating an image signal from a sampled signal generated by the sampling circuit, wherein
  the step of generating the image signal generates a digital brightness signal of a frequency smaller than that of the sampling rate by adding contiguous digital values contained in the sampled signal on a predetermined number by predetermined number digital value basis and divides each digital value of the generated digital brightness signal so that the number of bits of the generated digital brightness signal becomes equal to that of digital values of the sampled signal to generate an image signal in which each digital value of the divided digital brightness signal constitutes one pixel data.

6. The image generation method using a scanning electron microscope according to claim 5, wherein the step of generating the image signal sets the frequency of the digital brightness signal so that a period of the digital brightness signal does not change even if the sampling rate changes.

7. A scanning electron microscope; comprising:
a scan deflector for performing a scan of an electron beam on a sample surface;
an objective lens for focusing the electron beam on the sample surface;
a secondary electron detector for detecting secondary electrons or backscattered electrons from the sample to generate an analog brightness signal;
an AD converter for sampling the analog brightness signal at a predetermined sampling rate; and
a digital signal processing circuit for generating an image signal from a sampled signal generated by the AD converter, wherein
the digital signal processing circuit generates a digital brightness signal of a frequency equal to 1/N of that of the sampling rate by adding contiguous digital values contained in the sampled signal on a N by N digital value basis, and divides each added digital value of the sampled signal by N so that a number of bits of the generated digital brightness signal becomes equal to that of digital values of the sampled signal to generate an image signal in which each digital value of the divided digital brightness signal constitutes one pixel data.

8. The scanning electron microscope according to claim 7, wherein the digital signal processing circuit sets the frequency of the digital brightness signal so that a period of the digital brightness signal does not change even if the sampling rate changes.

* * * * *